United States Patent
Hermannsson

(10) Patent No.: US 8,025,539 B2
(45) Date of Patent: Sep. 27, 2011

(54) CONNECTOR FOR BIOMETRIC BELT

(75) Inventor: Kormakur Hermannsson, Reykjavik (IS)

(73) Assignee: Nox Medical EHF., Reykjavik (IS)

( * ) Notice: Subject to any disclaimer, the term of this patent is extended or adjusted under 35 U.S.C. 154(b) by 0 days.

(21) Appl. No.: 12/781,572

(22) Filed: May 17, 2010

(65) Prior Publication Data

US 2010/0297868 A1   Nov. 25, 2010

(51) Int. Cl.
*H01R 4/48* (2006.01)

(52) U.S. Cl. ........................................... 439/860

(58) Field of Classification Search .................. 439/860, 439/859, 909
See application file for complete search history.

(56) References Cited

U.S. PATENT DOCUMENTS

| | | | |
|---|---|---|---|
| 5,326,272 A * | 7/1994 | Harhen et al. | 439/86 |
| 7,171,265 B2 * | 1/2007 | Hoium et al. | 607/2 |
| 7,914,350 B1 * | 3/2011 | Bozich et al. | 439/822 |
| 2007/0167089 A1 * | 7/2007 | Gobron et al. | 439/860 |

* cited by examiner

*Primary Examiner* — Phuong K Dinh
(74) *Attorney, Agent, or Firm* — Birch, Stewart, Kolasch & Birch, LLP.

(57) ABSTRACT

A biometric belt connector for electrically connecting an electrode belt to a biometric device to be carried on a human or animal body. The belt connector comprises a back element and a front element configured to engage with each other in a fixed and locked arrangement, fastening in between them an end of an electrode belt, the front element having a substantially circular hole, an electrically conducting wire which forms a loop, such that part of said wire loop is exposed through said hole when the back and front elements are engaged. The wire loop is connected to a conducting element extending from an end of an electrode belt, which conducting element forms part of or is connected to an electrode in the electrode belt. The hole is of suitable dimension to form a female snap button receiver for a male snap fastener on said biometric device.

10 Claims, 4 Drawing Sheets

CONNECTOR FOR BIOMETRIC BELT

FIELD OF INVENTION

The present invention is within the field of medical devices, in particular biometric devices for measuring biosignals, and relates particularly to electrodes for such devices and in particular electrode belts and connectors for such belts.

BACKGROUND

Electrode belts are known, both for direct contact galvanic electrodes for measure cardiography signals and inductive belts used in respiratory inductive plethysmography. Prior art belts have various types of connectors, for transmitting the received signal to the respective device. There remains a need for improved belt connectors that are easy to use to maintain.

SUMMARY OF INVENTION

The invention provides a belt connector for electrically connecting an electrode belt 8 to a biometric device to be carried on a human or animal body. The belt connector comprises a back element 2, a front element 3, which back and front elements are configured to engage with each other in a fixed and locked arrangement, when the connector is assembled and ready for use. In between the front and back element is fastened an end 7 of the electrode belt 8. The front element has a substantially circular hole 4, and inside the connector is an electrically conducting wire which forms a loop 5, such that part of said wire loop is exposed through the hole 4 when the back and front elements 2,3 are engaged. The wire loop is connected to a conducting element 6 extending from the end of the electrode belt, which conducting element forms part of or is connected to an electrode in said electrode belt 8, the hole 4 being of suitable dimension to form a female snap button receiver for a male snap fastener on said biometric device.

DETAILED DESCRIPTION

Figure 1A:
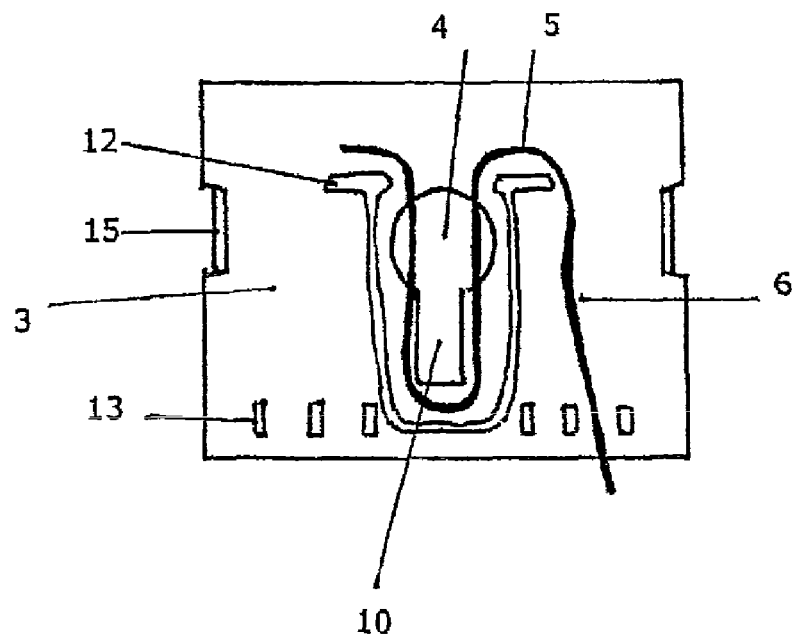
FIG. 1 illustrates the back element 3 (FIG. 1*a*) and front element 2 (FIG. 1*b*) of the belt connector before assembly.

The disclosed belt connector is suitable for various types of electrode belts, such as for cardiographic measurements, both in clinical settings or for training purposes, but also for belts such as RIP (respiratory inductive plethysmography) belts.

The belt connector is made from any of various suitable non-conducting materials, most preferably plastic, such as polyethylene, e.g. low density polyethylene (LDPE) or high density polyethylene (HDPE), or derivatives such as polyethylene terephthalate (PET) or polyfluoroethylene (PTFE), or more preferably polypropylene.

The belt connector is suitably provided in a pair of two, with one connector to be fastened on each end of an electrode belt, and where the biometric device fastens to both connectors, thereby holding together the belt in a loop. The two connectors can have essentially symmetrical fasteners, or they can be asymmetric, if it is desired to have a dedicated "left" and "right" end on the belt, always mounted on the same side of the device and/or the body.

Any of various conventional means can be used to make the length of the belt adjustable, e.g. by fastening surplus belt length to the main surrounding a body of a subject with a simple plastic clip, or by velcro type hook and look fastening strips attached at suitable location on the belt.

The belt connector comprises a back element and a front element, which back and front elements are configured to engage with each other in a fixed and locked arrangement, fastening in between them an end of said electrode belt. The front element is defined as the element forming the side of the connector facing outwardly from a subject's body when the belt is mounted, thus the front element side is also the side facing a biometric device to be connected to the belt.

The front and back elements can in one embodiment be formed in a single piece, e.g. held together with a hinge-like joint, or the front and back elements can also formed as two separate pieces. The two pieces can be glued together, melted, engaged with hooks and engaging loops or any combination of such means. Typically, the connector is meant to be engaged permanently and not to be disassembled.

As mentioned, the front element of the connector has a substantially circular hole of suitable dimension to form a female snap button receiver for a corresponding male snap fastener on the biometric device. An electrically conducting wire inside the connector forms a loop, such that part of said wire loop comes in contact with the male snap fastener when inserted in the hole, forming an electrical connection. Thus, the wire loop is generally slightly exposed. Preferably the loop is shaped so as to form a spring mechanism or clamp, that clamps to form a tight contact with the male fastener, ensuring good electrical contact. A conventional male snap fastener has a wide head portion and a narrower neck portion and the female snap fastener should preferably have a clamp arrangement to clamp around the neck portion of the male fastener with spring action, such that the female fastener is securely fastened but can be removed with some force. In one embodiment, two substantially parallel portions of the wire loop form part of a spring snap mechanism of the female snap button receiver. The wire loop is connected to a conducting element extending from said end of the electrode belt, and the conducting element forms part of or is connected to an electrode in the electrode belt, however the wire itself can also simply extend and form itself the conducting element.

The part of the wire loop which contacts the male fastener must however not form direct contact with skin which touches the outside of the hole, such as a human finger lightly touching the connector.

In a preferred embodiment the hole has an extension to provide an extended opening, such that the main hole itself forms a female snap button receiver as mentioned, while the extension provides an additional opening for a mating male projection on the biometric device. By this arrangement it is assured that the device cannot be incorrectly fastened, and the device will not fit any generic non-proprietary belts having connectors with female fasteners but without the correctly shaped and placed extended hole.

The connector has in another embodiment a separate further hole, not joined to the main fastener and electrical connection hole, where the further hole can mate with a corresponding male projection on said biometric device. Alternatively, the biometric device can have a hole for mating with a corresponding male projection on the belt connector.

It is an advantage in some embodiments of the connector that the hole is configured to allow moisture to escape from within the assembled connector. The connector may also have other separate one or more holes for allowing trapped moisture to escape from within the connector. Preferably such breathing holes are small enough to prevent dust and smudge to enter. Such further holes can be made as partitions in a hinge portion holding together the front and back element as described above.

In one embodiment the back element has a dimple shape which is placed beneath the main connecting hole, when the front and back elements are engaged to form the belt connector, such that the dimple receives the head portion of the male snap fastener.

Preferred Embodiment

Figure 1B:
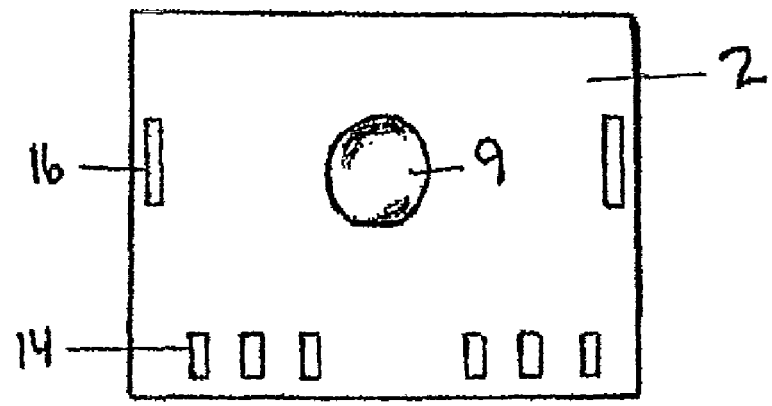
Figure 2:
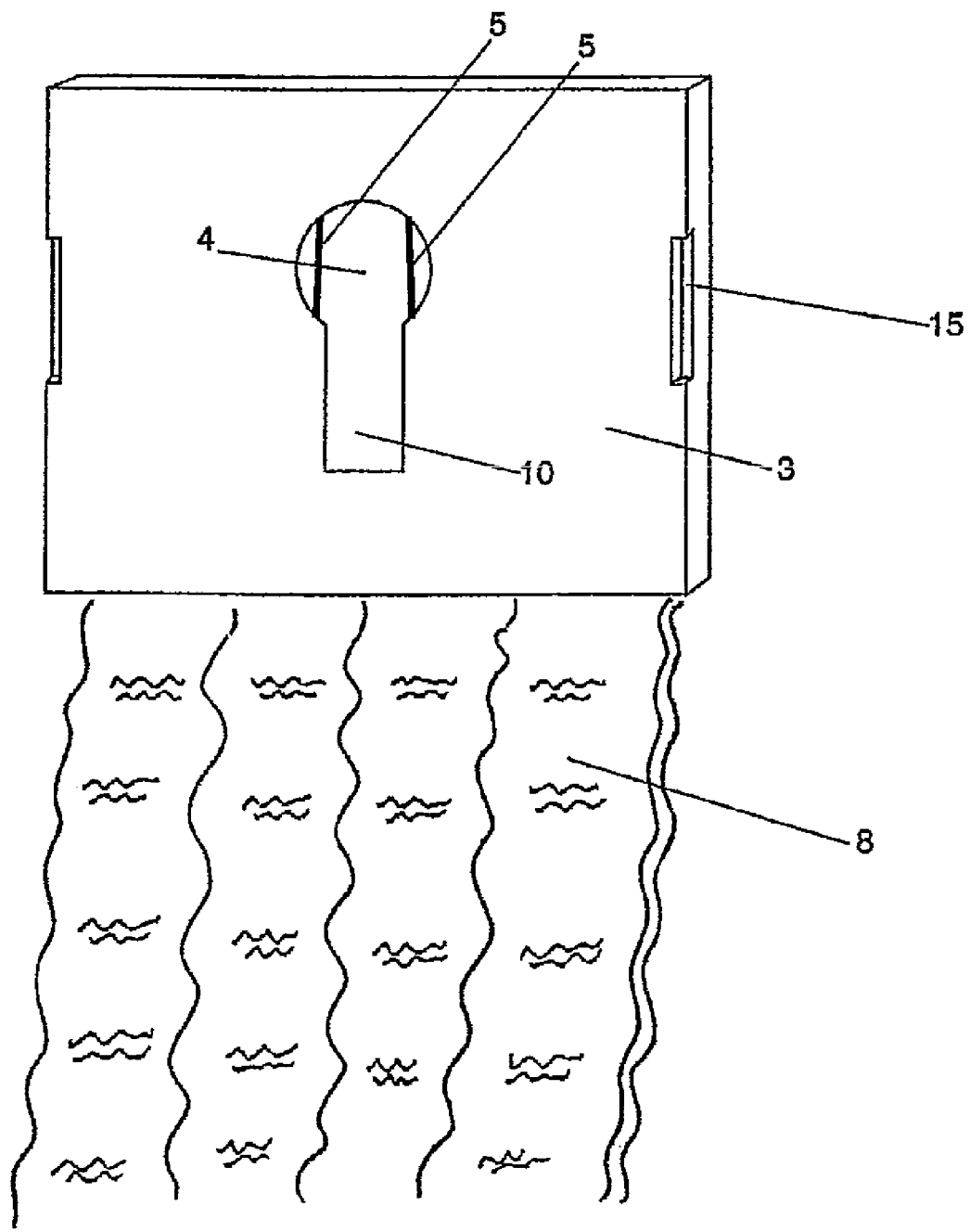
FIG. 2 shows the assembled belt connector with attached electrode belt 8.

FIG. 1 illustrates the front and back element of one embodiment of the connector (FIGS. 1a and 1b respectively) seen from the inside. Proper placement and location of the wire loop 5 is guided by an extending ridge 12 molded in the element piece. The extending ridge 12 comprises two small wings 19 (shown in FIGS. 3a, 3b and 5) that hold the wire loop in suitable proximity to the hole. The loop is shaped such that two parallel pieces thereof lie over the hole 4, such that these loop sections will be exposed and visible from the outside through the hole, as shown in FIG. 2. An extended hole 10 extends from main hole 4, forming a keyhole-like shape. Teeth 13 match corresponding notches 14 on the back element to hold firmly the end of a belt 8 when inserted between the engaged front and back elements. Clasp elements 15 are shown in this embodiment, which engage with notches 16 to keep the two parts together.

FIG. 2 shows the assembled connector, with portions of the wire 5 exposed inside the hole 4, forming part of a spring snap mechanism of a female snap button receiver. Electrode belt 8 extends from the connector.

Figure 3:
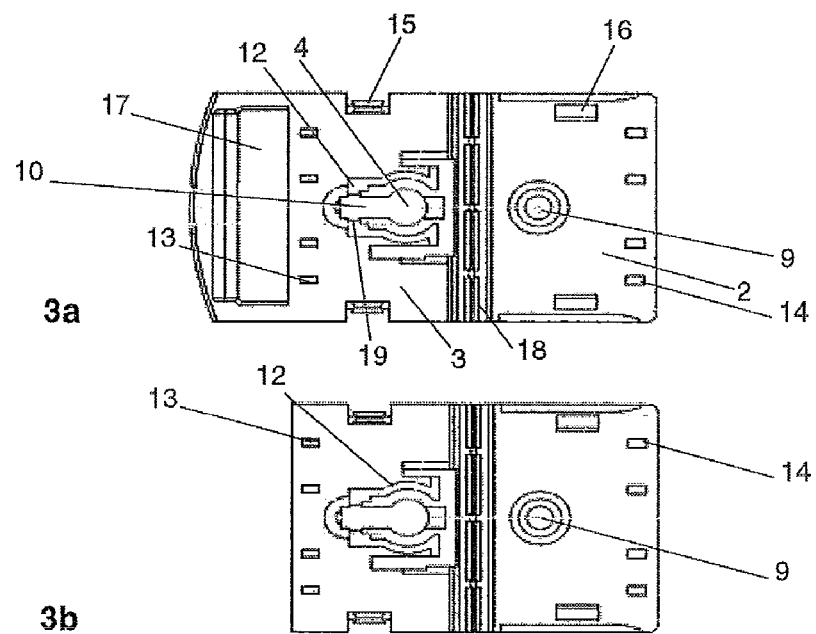
FIG. 3 shows the inside faces of a front element 2 and back element 3 joined together with a hinge 18.

FIG. 3 shows the inside faces of the connector where the front side and back side are joined with a hinge 18. FIG. 3a shows a connector with a belt adjusting opening 17.

Figure 4:
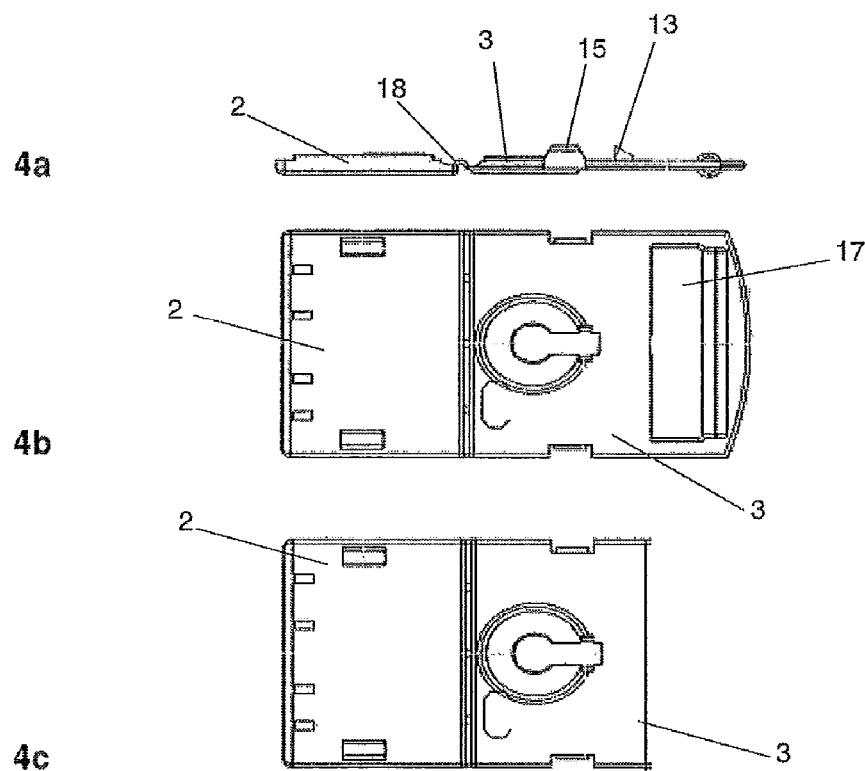
FIG. 4 shows the outside faces of a front element 2 and back element 3 joined together with a hinge.

FIG. 4 shows the same belt connector, showing the outside faces and a side view (top). 4a shows a side view, and 4b and 4c the connector with and without a belt adjusting opening, respectively.

Figure 5:
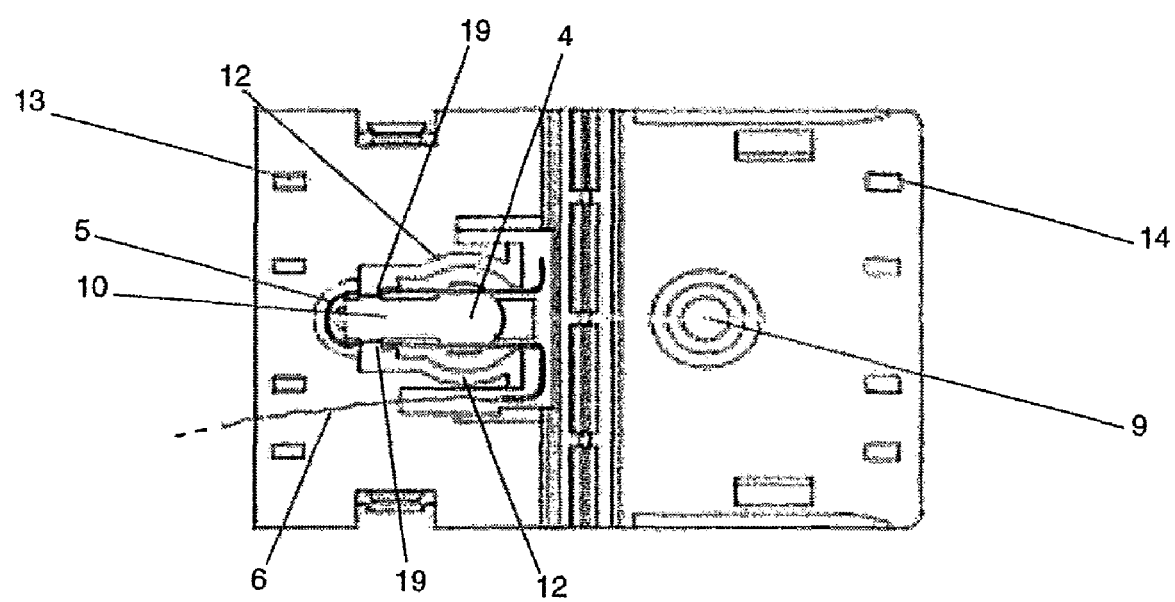
FIG. 5 shows the inside faces of a front element 2 and back element 3 joined together with a hinge 18, with a wire loop 5 mounted and held in place by the extending ridge 12 and wings 19.

FIG. 5 shows how the wire loop 5 is held in place by the extending ridge 12 and small wings 19. Also, the circular protrusion forming the dimple 9 presses against the wire loop, ensuring that the parallel wire legs forming the female snap fastener, are held substantially in the same plane within the assembled belt connector.

The invention claimed is:

1. Biometric belt connector (1) for electrically connecting an electrode belt (8) to a biometric device to be carried on a human or animal body, the belt connector comprising:
    a back element (2), a front element (3), which back and front elements are configured to engage with each other in a fixed and locked arrangement, fastening in between them an end (7) of said electrode belt (8),
    said front element having a substantially circular hole (4),
    an electrically conducting wire which forms a loop (5), such that part of said wire loop is exposed through said hole (4) when the back and front elements (2,3) are engaged,
    said wire loop being connected to a conducting element (6) extending from said end of said electrode belt (8), which conducting element forms part of or is connected to an electrode in said electrode belt (8),
    the hole (4) being of suitable dimension to form a female snap button receiver for a male snap fastener on said biometric device.

2. The belt connector of claim 1, wherein two substantially parallel portions of said wire loop (5) are exposed through said hole, forming part of a spring snap mechanism of said female snap button receiver.

3. The belt connector of claim 1, wherein said back element has a dimple (9), placed beneath said hole (4), when the front and back elements are engaged to form the belt connector, such that said dimple receives said male snap fastener.

4. The belt connector of claim 1, wherein said loop (5) does not form direct contact with skin, such as a human finger, lightly touching the hole (4).

5. The belt connector of claim 1, wherein said front and back elements are formed in a single piece held together with a hinge-like joint.

6. The belt connector of claim 1, wherein said front and back elements are formed as two separate pieces.

7. The belt connector of claim 1, wherein said hole (4) is configured such that it allows moisture to escape from within the assembled connector.

8. The belt connector of claim 1, wherein said hole (4) has an extension (10), to provide an extended opening, such that the hole (4) forms a female snap button receiver, while the extension (10) provides an additional opening for a mating male projection on said biometric device.

9. The belt connector of claim 1, wherein said front piece has a further hole (11) for a mating male projection on said biometric device.

10. The belt connector of claim 1, wherein said assembled connector has further one or more holes for allowing trapped moisture to escape from within the connector.

* * * * *